US012697508B2

(12) United States Patent
Engel

(10) Patent No.: US 12,697,508 B2
(45) Date of Patent: Aug. 4, 2026

(54) COMPUTER-IMPLEMENTED METHOD FOR USE IN DETERMINING A RADIATION DOSE DISTRIBUTION IN A MEDICAL VOLUME

(71) Applicant: Siemens Healthcare GmbH, Erlangen (DE)

(72) Inventor: Klaus Engel, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 692 days.

(21) Appl. No.: 18/157,199

(22) Filed: Jan. 20, 2023

(65) Prior Publication Data

US 2023/0233877 A1      Jul. 27, 2023

(30) Foreign Application Priority Data

Jan. 24, 2022    (EP) .................................... 22152982

(51) Int. Cl.
*A61N 5/10*          (2006.01)
*G06T 15/08*        (2011.01)

(52) U.S. Cl.
CPC ............ *A61N 5/1031* (2013.01); *G06T 15/08* (2013.01); *A61N 2005/1034* (2013.01); *A61N 2005/1035* (2013.01); *G06T 2210/41* (2013.01)

(58) Field of Classification Search
CPC .................. A61N 5/103; A61N 5/1031; A61N 2005/1034; A61N 2005/1035; G06T 15/08; G06T 2210/41
See application file for complete search history.

(56) References Cited

U.S. PATENT DOCUMENTS

| | | | | |
|---|---|---|---|---|
| 9,486,644 | B2 * | 11/2016 | Sobotta | ................ A61N 5/1031 |
| 10,347,032 | B2 * | 7/2019 | Engel | ....................... G06T 15/08 |
| 10,555,709 | B2 * | 2/2020 | Sossong | ............... A61N 5/1067 |
| 11,439,846 | B2 * | 9/2022 | Vik | ...................... A61N 5/1031 |
| 2010/0104068 | A1 | 4/2010 | Maurer, Jr. et al. | |
| 2010/0183121 | A1 | 7/2010 | Riker et al. | |
| 2017/0294042 | A1 | 10/2017 | Engel | |

* cited by examiner

*Primary Examiner* — An H Do

(74) *Attorney, Agent, or Firm* — Harness, Dickey & Pierce, P.L.C.

(57)          ABSTRACT

A computer-implemented method for use in determining a radiation dose distribution in a medical volume, includes: receiving a volumetric dataset representing the medical volume; performing a selection process of a rendering process for generating a visualization of the volumetric dataset to select at least one sample point in the volumetric dataset on which to perform a radiation determination process; and performing, for the at least one sample point in the volumetric dataset, the radiation dose determination process to determine a radiation dose at the at least one sample point. The method may also include visualizing the volumetric dataset and/or the radiation dose distribution.

26 Claims, 6 Drawing Sheets

Fig 1

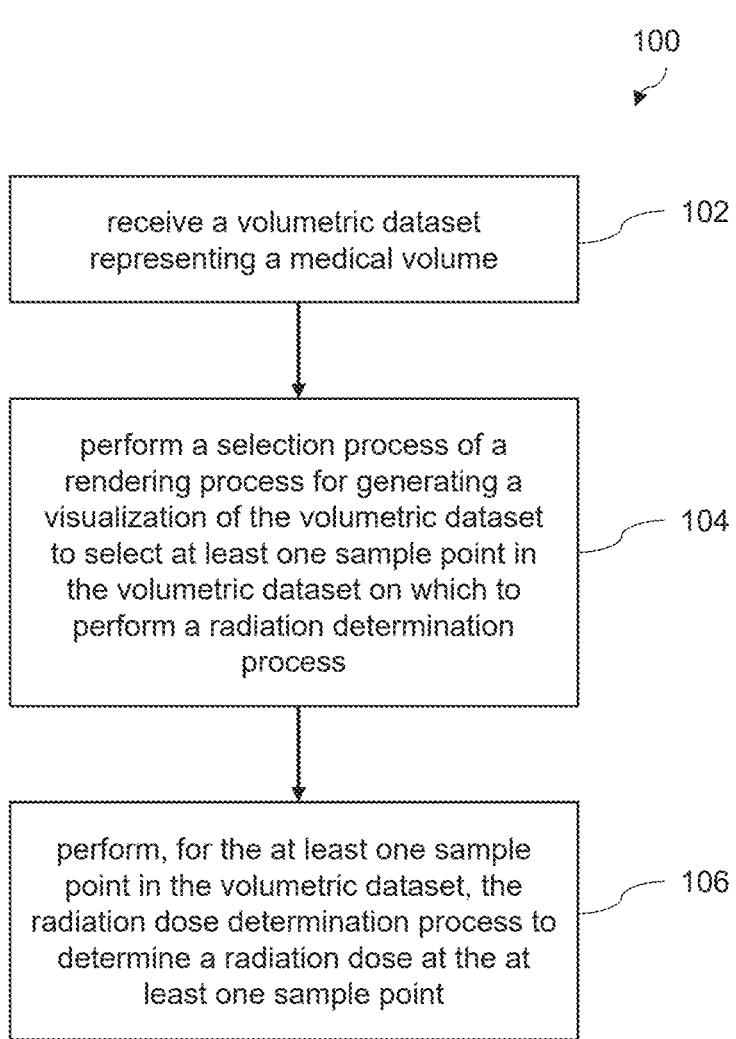

100 receive a volumetric dataset representing a medical volume — 102 perform a selection process of a rendering process for generating a visualization of the volumetric dataset to select at least one sample point in the volumetric dataset on which to perform a radiation determination process — 104 perform, for the at least one sample point in the volumetric dataset, the radiation dose determination process to determine a radiation dose at the at least one sample point — 106

COMPUTER-IMPLEMENTED METHOD FOR USE IN DETERMINING A RADIATION DOSE DISTRIBUTION IN A MEDICAL VOLUME

CROSS-REFERENCE TO RELATED APPLICATION(S)

The present application claims priority under 35 U.S.C. § 119 to European Patent Application No. 22152982.9, filed Jan. 24, 2022, the entire contents of which are incorporated herein by reference.

FIELD

One or more example embodiments of the present invention relate to a computer-implemented method for use in determining a radiation dose distribution in a medical volume.

BACKGROUND

In radiation therapy, computer-generated simulations can be used to plan the radiation dose to be applied to a patient.

For example, a medical scan methodology, e.g. CT scanning, may be used to obtain volumetric scan data representing the patient, or a portion of the patient. A physics simulation may then be performed using the volumetric scan data to simulate the application of radiation to the patient. Treatment parameters such as radiation source types, positions, directions, beam energy, collimators, etc. may be set and used to define the simulation. The simulation may, for example, involve a Monte Carlo method.

The results of such a simulation are typically in the form of a dataset containing calculated radiation dose values on a voxel-by-voxel basis throughout the volumetric scan data representing the patient volume. Such a dataset may be referred to, for example, as a radiation dose volume data set or a radiation dose map.

In order to visualize the application of the simulated dose to the patient, a suitable rendering technique may be used. For example, the volumetric scan data representing the patient and the radiation dose map may be provided to a rendering module which fuses the scan data and the radiation dose map into a single 2D/3D image. For instance, a color palette may be used to represent computed doses from the radiation dose map. The patient scan volume may then be rendered by a volume rendering technique with the rendered image being colorized according radiation dose map.

SUMMARY

According to a first aspect of an embodiment of the present invention there is provided a computer-implemented method for use in determining a radiation dose distribution in a medical volume, the method comprising: receiving a volumetric dataset representing the medical volume; performing a selection process of a rendering process for generating a visualization of the volumetric dataset to select at least one sample point in the volumetric dataset on which to perform a radiation determination process; and performing, for the at least one sample point in the volumetric dataset, the radiation dose determination process to determine a radiation dose at the at least one sample point.

The selection process of the rendering process may comprise determining one or more paths through the volumetric dataset for use in the rendering process and selecting one or more points along each of the one or more paths as respective sample points of the at least one sample point.

The path may be determined according to a physically-based path tracing process. The path may be determined according to a ray casting process.

The radiation dose determination process may comprise determining a radiation dose contribution at the sample point from each of one or more respective radiation sources located at respective pre-determined positions with respect to the volumetric dataset.

The determining of the radiation dose contribution at the sample point from a given one of the radiation sources may comprise simulating an arrival at the sample point of attenuated radiation from the given radiation source.

Determining the dose contribution from a or the given one of the radiation sources may comprise simulating radiation arriving at the sample point from the given radiation source by one or more scattered radiation paths.

The radiation dose determination process may comprise determining the dose contribution at the sample point based on a pre-computed dose map associated with the volumetric dataset.

The method may comprise performing the rendering process to render a visualization of the volumetric dataset and/or the radiation dose distribution including the radiation dose at a plurality of sample points including the least one sample point.

A sampling resolution of the plurality of sample points may be equal to a sampling resolution of the rendering process.

The rendering process may comprise determining a visual parameter value for the sample point for use in the rendering process, based on one or more of: the determined radiation dose at the sample point; a value of the volumetric dataset at the sample point; and a segmentation associated with the sample point.

The rendering process may comprise determining, based on the determined radiation dose at the sample point, a radiation dose visualization parameter value associated with the sample point; determining, based on a value of the volumetric dataset at the sample point, a volume visualization parameter value; and combining the radiation dose visualization parameter value and the volume visualization parameter value to determine the visual parameter value of the sample point.

The rendering process may comprise filtering, from the visualization, sample points at which the determined radiation dose is at or below a pre-determined threshold value.

The method may comprise determining, by performing the radiation dose determination process at a plurality of sample points selected by performing the selection process, a radiation dose distribution in the volumetric dataset, without computing a volumetric dose map for the volumetric dataset.

According to a second aspect of an embodiment of the present invention, there is provided a set of machine-readable instructions which when executed by a processor cause a method according to the first aspect of an embodiment of the present invention to be performed. According to additional aspects of embodiments of the present invention, there is a computer program product and/or a computer-readable medium comprising a set of machine-readable instructions which when executed by a processor cause a method according to the first aspect of an embodiment of the present invention to be performed.

According to a third aspect of an embodiment of the present invention, there is provided apparatus comprising a processor and a storage comprising a set of machine-readable instructions which when executed by the processor cause the processor to perform a method according to the first aspect of an embodiment of the present invention.

BRIEF DESCRIPTION OF THE DRAWINGS

The present invention will now be described, by way of example only, with reference to the following figures, in which:

FIG. 1 illustrates a flow chart representation of a method for use in determining a radiation dose distribution in a medical volume;

FIG. 5 is a flowchart representation of a method of determining visual parameter data for use in a rendering process according to examples described herein.

DETAILED DESCRIPTION

Figure 2:
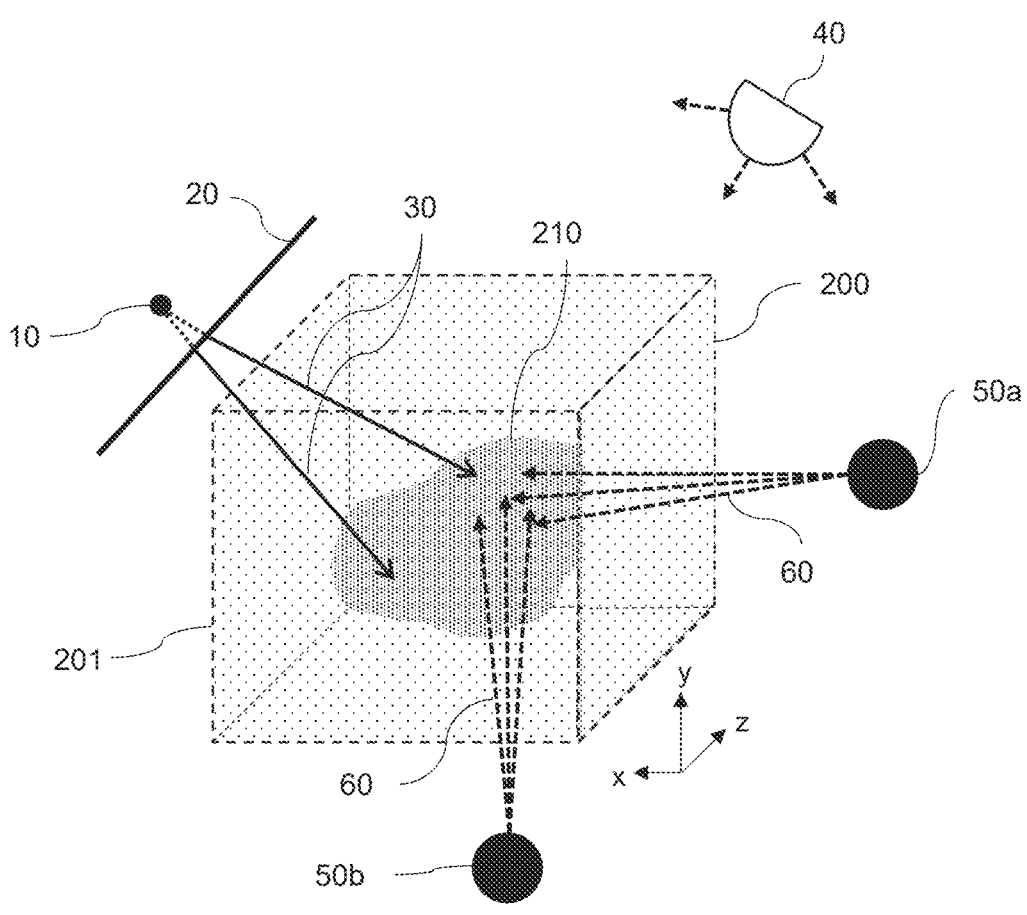
FIG. 2 illustrates schematically a volumetric dataset and an example of a method for use in determining a radiation dose distribution in the volumetric dataset according to examples described herein.

In certain examples described herein, a radiation dose determination process is performed at sample points in a volumetric dataset representing a medical volume, e.g. a CT or MR dataset. The sample points are selected by a selection process, which may also be referred to as a sampling process, of a rendering process for generating a visualization of the volumetric dataset and/or the radiation dose distribution. The rendering process may, for example, be a physically-based rendering process. A physically-based rendering process involves simulating light transport through a volume. In physically-based rendering, a plurality of light paths through the volumetric dataset may be determined by path tracing, e.g. using a Monte Carlo method. In order to visualize the volumetric dataset, visual parameter data, such as color and opacity, may be sampled at one or more points along each of the light paths. For example, the light paths may be sampled at pre-determined, e.g. equidistant, intervals. The data sampled at the sample points may be used to determine pixel display values, with a given light path contributing to the determination of a pixel display value for a given pixel with which the light path is associated.

In other examples, the rendering process may comprise a direct volume rendering process. Direct volume rendering process may involve casting a plurality of rays through the volumetric dataset to be rendered. Each of rays may be cast from a viewpoint through a given pixel in an image plane, and thus each ray may be associated with a given pixel in the image plane. Along a given ray, the volumetric dataset may be sampled at each of a plurality of sample points to obtain information for use in rendering a visualization of the volumetric dataset. For example, similarly to as described above for physically-based rendering processes, at each sample point, visual parameter data, such as color and opacity, may be determined from the volumetric dataset, e.g. by use of a transfer function. An integration of the visual parameter data of the sample points along a given ray may be determined to provide a pixel display value for the pixel with which the ray is associated. In this way, display values for the pixels in the image plane can be determined in order to provide an image for presenting to a user.

By using the selection process of a rendering process to select the sample points at which to perform the radiation dose determination process, the radiation dose determination process and the rendering process are made suitable for interleaving with one another. For example, the radiation dose determination process may be performed as a step in the rendering process allowing the radiation dose to be determined and visualized in an integrated manner. Further features and advantages of the present method will become apparent from the description below of certain examples.

FIG. 1 illustrates a flow chart representation of an example method 100 for use in determining a radiation dose distribution in a medical volume. The method comprises, at block 102, receiving a volumetric dataset representing the medical volume.

The volumetric dataset may comprise a discrete sampling of a scalar field. The volumetric dataset may be received by loading from a memory, sensors, and/or other sources. The medical volume represented by the volumetric dataset may represent a patient or a part of a patient, for example a human or animal patient. In general, any suitable scanning modality which will produce a volumetric dataset may be used to produce the volumetric dataset. For example, the scanning modality may comprise the use of computed tomography (CT), or of magnetic resonance imaging (MRI). In some examples a scanning modality comprising the use of positron emission tomography (PET), single photon emission computed tomography (SPECT), ultrasound, or another scan modality may be used. Scan data may be provided in the form of multiple two-dimensional (2D) scans or may be formatted from a scan. In some examples, the volumetric dataset is a DICOM dataset created by scanning at least a portion of a patient using a scanning modality.

The volumetric dataset may comprise data formatted as a plurality of voxels. The voxels may, for example, be in a uniform or non-uniform grid, or may be arranged in some other type of geometry (e.g., polar coordinate format). The voxels may be isotropic or anisotropic. Each voxel may typically represent a scalar value obtained by sampling a scalar field, although in some examples the volumetric dataset may comprise data relating to a non-scalar field. The type of value represented by each voxel may be dependent on the means or manner by which the volumetric dataset is obtained. For example, where a CT scanner is used to produce the volumetric dataset, the dataset may comprise Hounsfield values.

At block 104, the method comprises performing a selection process of a rendering process for generating a visualization of the volumetric dataset to select at least one sample point in the volumetric dataset on which to perform a radiation determination process.

The selection process may be a selection process of any rendering process suitable for rendering a visualization of the volumetric dataset. The selection process may, for example, comprise determining a path through the volumetric dataset and selecting, as the at least one sample point, a point along the path. A point of origination or termination of the path may, for example, be determined based on a viewpoint defined with respect to the volumetric dataset.

In some examples, the selection process may be a selection process of a physically-based rendering process. In such examples, the path through the volume along which the sample point is selected may be determined according to a path tracing process, for example a Monte Carlo path tracing process. To determine the path through the volumetric dataset, the path tracing process may, for example, simulate interactions of light rays with the volumetric dataset, e.g. using Woodcock tracking.

In other examples, the selection process may be a selection process of a direct volume rendering process, e.g. a ray casting process. In such examples, the path through the volume along which the sample point is selected may be determined by a ray casting, or ray marching approach.

The selection, as the sample point, of a point on the path through the volume may be performed according to a sampling process. For example, a sampling process may involve sampling the path through the volume at pre-determined, e.g. equidistant, intervals. In examples, a plurality of sample points may be selected by the selection process. In such examples, the selection process may comprise selecting, as the plurality of sample points, a respective plurality of points along a path through the volume. For example, the plurality of sample points may be selected according to a suitable sampling process, such as has been described above. In some examples, the sampling process may comprise 'jittering', in which, for example, the sample points may be initialized at equidistant points along the path with the location of individual respective sample points then being offset by a random small distance, e.g. using a Monte Carlo approach.

In some examples, the selection process comprises determining a plurality of paths through the volumetric dataset. The selection process may comprise selecting one or more points along each of a plurality of paths determined in accordance with a rendering process involving path tracing or a rendering process involving ray casting. Accordingly, a plurality of sample points may be selected, with each of the sample points being selected as a point on a determined path through the volumetric dataset. For example, the rendering process may comprise a path tracing process which involves tracing multiple paths through the volume, and the selection process may comprise selecting multiple sample points along each of the paths.

At block 106, the method comprises performing, for the at least one sample point in the volumetric dataset, the radiation dose determination process, to determine a radiation dose at the at least one sample point.

The radiation dose determination process may comprise determining the radiation dose by computing a respective radiation dose contribution at the sample point from each of one or more respective radiation sources. The radiation sources may be located at respective pre-determined positions with respect to the volumetric dataset.

The radiation sources may, for example, include one or more simulated radiation sources external to the volumetric dataset. For example, the radiation sources may include one or more external beam-like sources. Additionally, or alternatively, the radiation sources may include one or more sources located internally to the volumetric dataset. For example, the radiation sources may include one or more, e.g. omnidirectional, internal radiation sources for use in brachytherapy.

In some examples, determining the radiation dose contribution from a given radiation source comprises simulating the transport of the radiation through the volumetric dataset from the radiation source to the sample point. For example, the arrival of radiation at the sample point from the given radiation source may be simulated by determining the attenuation of radiation originating at the radiation source and arriving at the sample point. In one example, a ray marching approach may be used to simulate the attenuation of radiation along a ray joining the sample point and the radiation source. In some examples, the computation of the radiation dose contribution may take into account any one or more of dose absorption, emission, scattering, Bremsstrahlung and one or more other physical properties of the radiation.

Simulating the radiation dose contribution at the sample point from a given radiation source may comprise simulating various parameters of the radiation source. For example, an intensity, size, type, etc. of the radiation source may be defined for the simulation. Further features, such as, for example, collimators, in the case of beam-like sources, may also be accounted for in a simulation. Specific examples of determining the radiation dose at a sample point will be described below, with reference to FIG. 3.

In some examples, the radiation dose determination process may comprise determining the radiation dose from a pre-computed dose map. For example, a dose map may be pre-computed by a physics simulation performed on the volumetric dataset, e.g. by use of a Monte Carlo method. In such examples, at block 106, at the sample point, a radiation dose may be determined from the dose map, e.g. by interpolating dose values from the pre-computed dose map to obtain a dose value for the sample point.

As described above, the selection process may be performed to select a plurality of sample points. Where a plurality of sample points are selected by the selection process, the radiation dose determination process may be performed at each of the sample points to determine respective radiation doses for the sample points. Accordingly, the method 100 may be performed to determine a radiation dose distribution comprising radiation dose values at a plurality of sample points throughout the volumetric dataset.

In some examples, the method further comprises performing the rendering process to visualize the volumetric dataset and/or the radiation dose distribution. For example, the selection process of the rendering process may be performed as part of the rendering process, with the selection process being used to select sample points for use in generating a visualization of the volumetric dataset. In one such example, each of the sample points selected as described above may be sampling points selected as part of a path tracing process for generating a visualization of the volumetric dataset. In another example, each of the sample points is a point selected as part of a ray casting volume rendering process.

In an example rendering process, at each of the sample points, visual parameter data is determined for use in generating a visualization of the volumetric dataset and/or the radiation dose distribution. For example, at each sample point, volume visualization parameter data, such as an opacity and/or color, may be determined based on a value of the volumetric dataset at the sample point. For example, a transfer function may be used to determine an opacity and/or color at a given sample point based on an interpolated value of the volumetric dataset at the sample point. This may be referred to as classification of the volume data at the sample points. In some examples, a shading process may also be applied to obtain the volume visualization parameter data.

In an example rendering process according to the present disclosure, radiation dose visualization parameter data may be determined for the sample point, based on the determined radiation dose value for the sample point. For example, a dose color value may be determined based on the determined radiation dose value at the sample point. For example, a transfer function, e.g. a window-levelled transfer function, may be applied to the determined radiation dose value to determine radiation dose visualization parameter data for the sample point. The radiation dose visualization parameter data may comprise a dose color and, additionally or alternatively, values for visibility-related parameters (e.g. an opacity or alpha parameter) and parameters relating to material properties such as roughness, refraction, phase function etc.

During the rendering process, the visual parameter data which is assigned to a given sample point may be determined based on one or more of the volume visualization parameter data (e.g. color, opacity and other visualization information based on the classification of the sample point) and the radiation dose visualization parameter data (e.g. a color and/or other visualization information based on the determined radiation dose value at the sample point). For example, during the rendering process, to provide an opacity and color value for the sample point, an opacity and color determined by applying a transfer function to the volumetric dataset at the sample point may be blended with a dose color value based on the determined radiation dose at the sample point. The opacity and color resulting from this blending may then provide the opacity and color values to be used for the sample point in the rendering process.

During an example rendering process, this process of determining visual parameter data for a given sample point is performed at a large number of sample points along a given path and the visual parameter data at the sample points along the given path used to determine a contribution to a pixel display value for a pixel associated with the path. For example, to determine the contribution of a given path through the volume to the color of the pixel to which the path corresponds, the color of the sample points along the path may be blended. Accordingly, the contribution of the path to the pixel display value may depend at least in part on the dose colors at the sample points along the path. By using the radiation dose values, e.g. in addition to the classification of the volume at the sample points, as a basis for determining the visual parameter data for the sample points, the determined radiation dose values may be visualized by their effect on the pixel display values. For example, the rendering of the volume may be colorized according to a color palette representing the dose values.

In typical radiation therapy dose planning methods, the simulation of the dose and the visualization of the result are decoupled. For example, each time treatment parameters such as radiation source positions, directions, beam energy, collimator settings, etc. are changed, a simulation is started to generate a radiation dose distribution. The radiation dose distribution may then be visualized, e.g. by performing a rendering process on the volumetric dataset and merging the dose map with the rendered image by colorizing the rendered image according to the dose values of the dose map. This separation of the simulation and the visualization process means that the simulation of the dose distribution is decoupled from the rendering of the result. This may result in delays and low interactivity when changing system parameters, e.g. simulated radiation source types or positions. For example, the user may have to wait several seconds, minutes or even hours before a visualization of the dose is presented. This can result in a limitation of the interactive exploration of the system parameter space. Ultimately, for the patient, the consequence may be long waiting times between dose application sessions.

In contrast, according to the present method, a radiation dose distribution for a volumetric dataset is determined in a method which can be interleaved with a rendering process. That is, radiation dose values are determined at sample points selected by the selection process of a rendering process and, therefore, the determination of the radiation dose values can conveniently be performed as part of the rendering process. This allows for the determining of a radiation dose distribution and the rendering of a visualization of the volumetric dataset and/or the radiation dose distribution to be integrated into a single process, an example of which is described below with reference to FIGS. 2 and 3. Accordingly, the simulation of the dose and the rendering of the results can, for example, be performed in the same computation module.

According to examples of the present method, the determined dose distribution and the visualization of the volume and the dose distribution can be progressively refined over time. For example, as more paths are determined according to the rendering process, more radiation dose values may be determined. This permits the interactive change of parameters with the immediate refinement, and optionally, visualization, of the dose simulation. In certain examples, the method may be considered an image space method. That is, the output may be a 2D pixel image that shows a rendered projection of the volumetric dataset with the radiation dose distribution being visualized by its effect in colorizing pixels in the 2D pixel image.

Since the sample points at which the radiation dose values making up the radiation dose distribution are computed may be the same sample points as those sampled to visualize the volumetric dataset using the rendering process, the radiation dose distribution may be computed at a resolution similar to or the same as that of the rendering. Moreover, the radiation dose values are computed at sample points which are determined according to a rendering process for rendering an image and may, be computed only at these sample points. Accordingly, if desired, the radiation dose may be computed for the image to be rendered without computing a volumetric dose map for the volume. This can allow for a lower memory footprint and quicker visualization of a radiation dose distribution since no radiation dose volume need be generated and the dose computations may be computed in image space and interleaved in the rendering process.

The method also provides for a 3D dose volume to be computed, if desired. For example, in order to compute a dose volume, a radiation dose distribution in the volumetric dataset may be computed in 2D image space slice-by-slice through the volumetric dataset. The values obtained by this slice-by-slice method may be used to form a dose volume, e.g. the slice-by-slice values may be voxelized.

Further, the method allows for a 4D simulated radiation dose distribution to be easily determined and visualized. For example, to produce a 4D radiation dose distribution a radiation dose distribution may be computed at each time step of the 4D volume data.

Various parameters of the simulation of the radiation dose may be adjusted, such as parameters defining the number, position, type and other features of the radiation sources, and the resulting radiation dose distribution determined. The method allows for efficient computation of the dose and allows for simulation parameters to be adjusted and quickly simulated and, optionally, visualized, allowing, for example, the effect of different parameters on the simulated radiation dose to be easily explored.

When employed in a progressive rendering approach, such as path tracing, the progressive nature of the computation means that the radiation dose computation accuracy is refined over time. For example, as the number of Monte Carlo paths increases with time and more sample points are evaluated, the dose computation accuracy is refined. Meanwhile, since the computation of the radiation dose may be performed during rendering, the dose distribution need not be pre-computed prior to the rendering process, in contrast with certain prior methods discussed above.

FIG. 2 illustrates schematically an example volumetric dataset 200 and aspects of examples according to the present disclosure. The volumetric dataset 200 may also be referred to as the volume 200. In this example, the volumetric dataset 200 comprises a representation of a portion 210 of a medical patient.

FIG. 2 illustrates an example rendering process for rendering a visualization of the volumetric dataset 200. In the example rendering process represented by FIG. 2, a viewpoint 10 is defined with respect to the volumetric dataset 200. A viewing plane 20 is also defined and located in front of the viewpoint 10. The viewing plane 20 comprises a plurality of pixels (not shown in FIG. 2), e.g. arranged in a grid, and allows construction of a visualization of the volumetric dataset 200, as viewed from the viewpoint 10.

To render a visualization of the volumetric dataset 200 as viewed from the viewpoint 10, a plurality of paths 30 through the volume 200 are determined and each of the paths is used to determine a light contribution to a given pixel in the viewing plane 20. According to the present example, the paths 30 are determined according to a physically-based path tracing method. However, in other examples, the paths 30 may be determined by a direct volume rendering approach, such as a ray casting approach. As described above, path tracing simulates light propagation through the volume 200, including simulating scattering and absorption, by tracing a plurality, for example millions, of simulated light paths 30. Each of the light paths 30 is used to generate an estimate of light hitting a given pixel in the image plane 20. The estimate for a given path 30 is determined by sampling the volume 200 at a plurality of sample points along the path, as will be described below with reference to the example shown in FIG. 3. By averaging many such estimates, an image is rendered on the image plane 20 and may be presented to a user.

According to an example, to create a single estimate of light hitting a pixel in the image plane 20, a light path 30 is traced from the viewpoint 10 through a given pixel in the image plane 20 and through the volume 200. An initial ray for the path 30 beginning from the viewpoint 10 is generated for a random position in a pixel on the image plane 20. The ray direction is determined by connecting this random position in the pixel with a random position on a simulated camera lens (not shown) at the viewpoint 10. The intersection of the ray, refracted by the camera lens, with a bounding box of the volume 200 is then computed and a scattering position (not shown) for the ray inside the volume 200 is determined, e.g. by Woodcock tracking.

The path 30 is then continued by determining a new ray originating at the scattering location. A direction of the new ray may, for example, be determined using a phase function, i.e. a probability density function for the scattering direction, at the scattering position. The phase function may, for example, be determined based on an interpolated value of the volumetric dataset 200 (e.g. a Hounsfield value where the volumetric dataset is produced by CT scanning) at the scattering position.

The new ray is traced in a similar manner to the initial ray to determine a next scattering position for the path 30, and the same operations are performed at the next scattering position as at the first scattering position. This path tracing process continues until a ray of the path 30 is absorbed by the volumetric dataset 200 or leaves the volumetric dataset

200. Absorption by the volumetric dataset 200 can be modelled, for example, either using a maximum threshold for the number of scattering events or probabilistically using an extinction probability density function based on the number of scattering events. In an example, if the path 30 is still inside the volume 200 after the maximum threshold number of scattering events, the path 30 makes no contribution to the detector pixel to which it corresponds. If the path 30 leaves the volume 200 within the given number of scattering events, a light contribution for the path 30 is determined and provides an estimate for light hitting the pixel to which the path 30 corresponds.

To determine the light contribution of a given path 30 to its associated pixel, the path 30 is sampled at a plurality of points along the path 30 (not shown in FIG. 2) and data is gathered at the sampled points to generate a contribution to a display value for the pixel associated with the given path 30. By generating many such paths 30 and determining their contributions to the display values of their associated pixels in the image plane 20, an image of the volume 200 is generated, e.g. with the image being progressively refined as the number of paths 30 traced increases.

In examples, a rendering algorithm may model an illumination effect by modelling a light source 40 illuminating the volume 200. The illumination effect may be taken into account when determining opacity and color values at the sample points. For example, a shading computation may be applied at the sample point, taking into account simulated light at the sample point. The light source 40 may be a point source, a directional light source, or may comprise a light map. The simulation light source may also be any other kind of light source—e.g. a model of any object which emits light- or a combination of multiple different light sources. In some examples, parts of the volumetric dataset 200 itself may emit light. In some examples, the light source may comprise a high definition light map. The light map may, for example, when the volume 200 is cuboidal, have six sides corresponding to outer sides of the volumetric dataset 200.

FIG. 2 also shows radiation sources 50*a*, 50*b*. In this example, the radiation sources 50*a*, 50*b* are simulated beam-like radiation sources positioned externally to the medical volume 200. The radiation sources 50*a*, 50*b* are arranged to irradiate the medical volume 200 with radiation 60 in order to simulate the application of a radiation dose to the portion 210 of the medical patient. For example, the portion 210 may comprise a tumor to be treated by radiation therapy and the simulation may be used to plan the number, type, position, etc. of radiation sources to be used in the radiation therapy.

According to an example of the present method, at each of the plurality of sample points along the paths 30 generated for the volume rendering, a radiation dose value is computed. Computing the radiation dose value at a given sample point comprises computing a radiation dose contribution at the sample point from each of the radiation sources 50*a*, 50*b*. In examples, the data gathered at the sample points along the paths 30, on the basis of which the respective light contributions for the paths 30 are determined, comprises the radiation dose values at the sample points. The pixel display values for the image plane 200 may be based on the determined radiation dose values for the sample points, e.g. in addition to the interpolated volume data at the sample points. Accordingly, the radiation dose distribution may be visualized in the image of the volumetric dataset 200 produced at the image plane 20.

Figure 3:
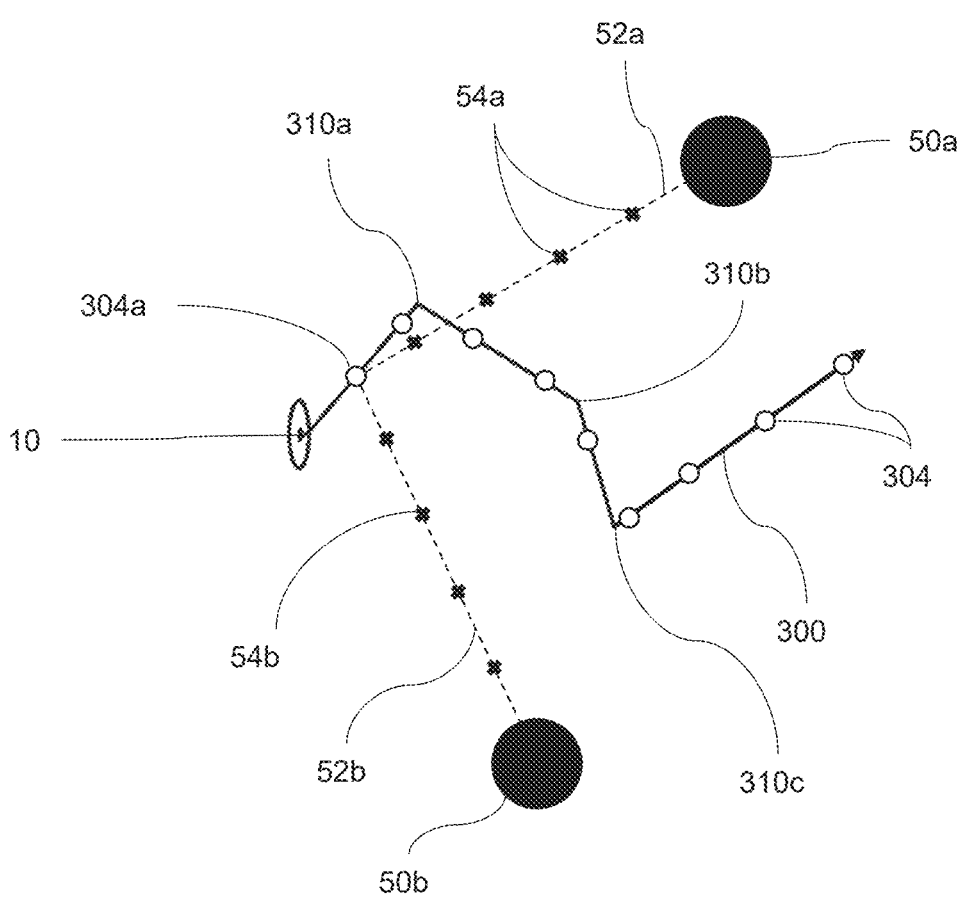
FIG. 3 illustrates schematically aspects of the example method of FIG. 2.

FIG. 3 shows an example path 300 of the paths 30 of FIG. 2 through the volumetric dataset 200. In this example, the path 300 interacts with the volumetric dataset 200 at first, second and third interaction points 310a, 310b, 310c respectively. The locations of the interaction points 310a, 310b, 310c may, for example, be determined via Woodcock tracking, while the change in direction of the path 300 at a given interaction point 310a, 310b, 310c, may be determined via a scattering probability density function, as has been described above.

As part of the rendering process, along the path 300, a plurality of sample points 304 are selected (only some of which are labelled in FIG. 3, for clarity), e.g. by sampling the path 300 at regular equidistant intervals, for example, of around one sampling point per voxel, or around two or more sampling points per voxel. At each of the plurality of sample points 304 along the path 300, volume visualization parameter data, such as an opacity and a color, are assigned. The volume visualization parameter data may, for example, be determined by use of a transfer function which assigns volume visualization parameter data based on a scalar value of the volumetric dataset 200 at a given sample point 304. The value of the volumetric dataset 200 at a given sample point 304 may, for example, be computed by interpolating voxel values of the volumetric dataset 200 to determine a value of the volumetric dataset 200 at the given sample point 304. In some examples, additional properties related to a given sample point 304, such as a gradient of the volumetric dataset 200 at the sample point, may be used as an input into a transfer function.

In some examples, a transfer function may assign to a given sample point 304 one or more of: a scattering coefficient, a specular coefficient, a diffuse coefficient, a scattering distribution function, a bidirectional transmittance distribution function, and a bidirectional reflectance distribution function. These parameters may be used to derive any one or more of an opacity, reflectivity, surface roughness, or other properties at the sample point 304. These material properties may be derived based on scalar values of the volumetric dataset at the sample point 304, and/or based on user-specified parameters.

FIG. 3 shows a first example sample point 304a of the sample points 304, with reference to which an example radiation dose determination process for determining a radiation dose at the sample point will now be described.

The two radiation sources 50a, 50b of FIG. 2 are shown in FIG. 3. In the example of FIG. 3, the radiation dose at the sample point 304a is determined by determining respective radiation dose contributions from the radiation sources 50a, 50b. In this example, a ray marching approach is used to simulate the attenuation of radiation arriving at the sample point 304a from the radiation sources 50a, 50b.

In this example, to simulate radiation arriving at the sample point 304a from the first radiation source 50a, a radiation ray 52a is computed which connects a random position on the first radiation source 50a to the sample point 304. For the radiation ray 52a, a dose contribution value is initialized to an energy of the first radiation source 50a. The ray is then traversed, from the position on the first radiation source 50a to the sample point 304a. The energy of the first radiation source 50a may form a parameter of the simulation to be set by a user.

Following the initialization of the energy of the first radiation source 50a, ray marching is performed towards the sample point 304a. This involves selecting a plurality of ray marching sample points 54a (only some of which are labelled in FIG. 3, for clarity) along the radiation ray 52a. The selecting of the plurality of ray marching sample points 54a may involve any suitable sampling process, e.g. sampling the ray 52a at equidistant intervals. In some examples, the selecting of the plurality of ray marching sample points 54a comprises Monte Carlo sampling. For example, the plurality of ray marching sample points 54a may be initialized to be at equidistant intervals along the ray 52a. A Monte Carlo method may be used to offset each of the sample points 54a by a respective random small distance. This approach may be referred to as 'jittering' and can help to avoid artefacts which may occur when sampling at regular intervals. As mentioned above, jittering may also be applied when selecting the sample points 304.

At each of the ray marching sample points 54a a respective value of the volumetric dataset 200 is determined, e.g. by interpolating the volume data. The determined value of the volumetric dataset 200 is then mapped to a local physical radiation attenuation value. This mapping may, for example, be based on a physical model relating the volume value (which may be representative of a density of the volume, e.g. when the volumetric dataset is a CT dataset) to the level of attenuation provided by the volume to the radiation from the first radiation source 50a.

Alternatively, or additionally, the local physical radiation attenuation value for the sample point 54a can be determined based on a segmentation of the volumetric dataset 200 at the sample point 54a. For example, a material type segmentation volume may be defined and at a given sample point 54a a lookup may be performed for the material type at with the sample point 54a. For example, the segmentation may define the type of organ or anatomical tissue at the sample point 54a. A local physical radiation attenuation value for the sample point may then be determined based on the material type, e.g. according to a physical model modelling attenuation of radiation in the material type.

Once the local physical radiation attenuation value for the sample point 54a is determined, this value is applied to attenuate the dose contribution value for the first radiation source 50a, which, as above, is initialized to the energy of the radiation source 50a at the beginning of the ray marching process. The process of determining a local physical radiation attenuation value is performed at each of the sample points 54a along the ray 52a. An accumulated attenuation value representing the amount of attenuation provided to the energy of the first radiation source 50a along the ray 52a can be computed by integrating the local attenuation values at the sample points 54a along the ray. By applying this accumulated attenuation value to the energy of the first radiation source 50a, a dose contribution for the first radiation source 50a at the sample point 304a can be computed.

In some examples, Bremsstrahlung effects can also be simulated when determining the radiation dose contribution. For example, the dose contribution from the first radiation source 50a can be computed taking into account Bremsstrahlung effects by computing the depth into the material of the sample point 304a with respect to the first radiation source 50a, i.e, the distance which radiation from the first radiation source 50a must penetrate into the material to arrive at the sample point 304a, and, in addition to computing local radiation attenuation along the ray 52a in the manner described above, computing the attenuation of the dose contribution at the sample point 304a based on the depth of the sample point 304a with respect to the first radiation source 50a. The computation of the attenuation to the energy of the first radiation source 50a may, for example, in addition to an accumulated local attenuation value along the ray 52a, be based on a measured Bremsstrahlung curve or a physical model of Bremsstrahlung effects.

The same process used to determine the radiation dose contribution from the first radiation source 50*a* may be performed in respect of the second radiation source 50*b* to determine a radiation dose contribution at the sample point 304*a* from the second radiation source 50*b*. The radiation dose contributions from the first and second radiation sources 50*a*, 50*b*, and in other examples, any other radiation sources which are to be taken into account, are summed to obtain a total radiation dose at the sample point 304*a*.

In some examples, if, during the ray marching process, the attenuation of the dose contribution value at the sample point 304*a* from a given radiation source 50*a*, 50*b* is such that the dose contribution value falls below a given threshold, the ray marching may be terminated. This may be considered a form of performance optimization.

In some examples, the above-described ray marching approach may be applied only for radiation sources for which the sample point 304*a* is within a pre-determined radiation source influence area. For example, for a beam-like radiation source, a dose contribution may be computed only if the sample point 304*a* is within a beam of the radiation source. This can reduce the computational load of the method by not computing dose contributions from radiation sources which do not contribute a significant radiation dose at the sample point 304*a*.

In some examples, although this is not represented in FIG. 3, the determination of the dose contribution from a given radiation source 50*a*, 50*b* may take into account scattered radiation. For example, bidirectional path tracing may be used to compute one or more scattered paths from a given radiation source 50*a*, 50*b* to the sampling point 304*a*. For each of the scattered paths, an additional dose contribution for the radiation source 50*a*, 50*b* at the sample point may be computed, e.g. by using the same approach as that described above which is used to simulate radiation arriving by a direct path. The additional contribution/s from the one or more scattered paths may be added to the contribution from the direct path to obtain the total dose contribution from the radiation source 50*a*, 50*b* at the sample point 304*a*.

In some examples, more than one radiation path may be simulated to determine the radiation dose contribution from a given radiation source 50*a*, 50*b*. For example, for the first radiation source 50*a*, a plurality of rays similar to the ray 52*a* may be simulated, e.g. originating at different random positions on the first radiation source 50*a*. The dose contribution at the sample point 304*a* from the first radiation source 50*a* may then be determined based on (e.g. an average of) the dose contributions determined according to the plurality of different rays.

In examples, the determined total radiation dose at the sample point 304*a* is mapped to a dose color value. A mapping of radiation dose values to color values may be pre-defined, e.g., according to user preference. The dose color value for a given sample point 304 may then be blended with an opacity and color for the sample point 304*a* which is computed using a transfer function for rendering the volume 200. In some examples, the determination of the radiation dose values and dose color values at the sample point 304*a* can be inserted into a shader function of a rendering process. This may be done, for example, after classification of the sample point 304*a*, e.g. lookup of an RGBA for the sample point 304*a* from a transfer function.

The above-described process of determining radiation dose values and visual parameter data for the sample point 304*a* may be performed in respect of each of the sample points 304 along the path 300. By integrating the visual parameter data of the sample points 304 along the path 300, a contribution to the display values of the pixel with which the path 300 is associated can be determined. Where, at each of the sample points 304, the dose color is blended with the opacity and color obtained by classification of the volume 200, the contribution of the path 300 to the display values of the pixel depends on the radiation dose values along the path 300. Accordingly, the method may be used to integrate into the rendering process the determination of and visualization of the radiation dose values.

In some examples, if the determination of the dose color is performed after the evaluation of clipping planes in a rendering process, the rendering of the radiation dose distribution will not be influenced by clipping of the volume. Thus, a visualization may be generated showing clipping applied to the anatomy without the clipping being applied to the radiation dose visualization. For example, the clipped anatomy may be shown with a visualization of the radiation dose (based on the determined dose color) hovering in front of the clipped anatomy. In such examples, the visualization of the radiation dose may be mapped onto the anatomy, or rendered as a solid blob or as a semi-transparent cloud.

As mentioned above, in some examples, scattered radiation paths from the radiation sources 50*a*, 50*b* may be explicitly computed in the computation of the dose contribution from a given radiation source at the sample point 304. However, even if such scattered radiation paths are not explicitly computed, e.g. if only the direct path from the radiation source to the sample point is taken into account, a visual effect of scattered radiation may still be achieved. That is, since according to examples of the method, the radiation dose value modifies the color of a given sample point 304, various Monte Carlo paths through the volumetric dataset 200 generated during the rendering process may include samples colorized by a dose color at a given point in the volume 200. This effectively transports the dose color to other regions of the volume 200, which may, for example, include regions which are not directly in the influence zone of the radiation sources 50*a*, 50*b*.

Figure 4:
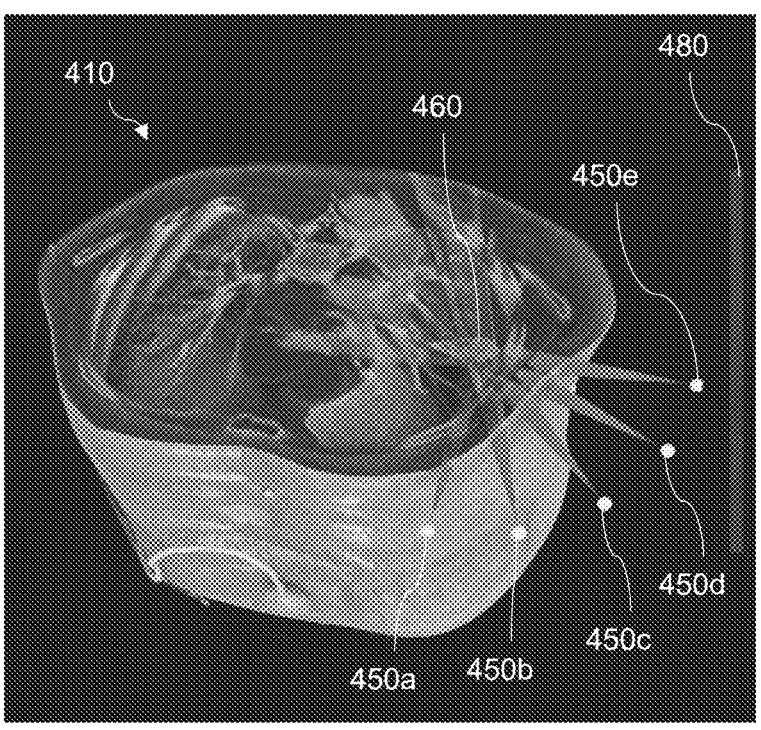
FIG. 4 shows an example visualization of a volumetric dataset and a radiation dose distribution in the volumetric dataset produced by a method according to examples described herein.

FIG. 4 shows an example visualization of a volumetric dataset and radiation dose distribution in the volumetric dataset produced by a method according to examples described above. The visualization shows an anatomical portion 410 being irradiated by beam-like radiation sources 450*a*, 450*b*, 450*c*, 450*d*, 450*e* located outside of the anatomical portion 410. Beams of the radiation sources 450*a-e* generally converge at a target area 460 in the anatomical portion 410. In this example the anatomical portion 410 is a chest cavity and the target area 460 contains a tumor to be targeted by radiation therapy. The visualization shows a dose color key 480 which shows the mapping between determined radiation dose values and dose colors applied in determining the visualization. FIG. 4 shows a result of radiation dose values, determined during rendering, being mapped to dose colors and those dose colors being blended with colors with opacities and colors determined via a transfer function applied to the volumetric dataset. The result is that the visualization of the anatomical portion 410 is colorized by the dose colors allowing the radiation dose values applied to different points in the anatomical portion 410 to be visualized.

Although this is not shown in FIG. 4, in some examples, the radiation dose values may be presented numerically in the image space. For example, the user may use a mouse of other pointing device to probe the image space and may be presented with radiation dose values for probed points in the image. For such examples, the visible dose can be computed in a 2D frame buffer which is separate to that of the 2D image of the volumetric dataset and the numerical result from the buffer for the pointing device position may be displayed to the user.

Figure 5:
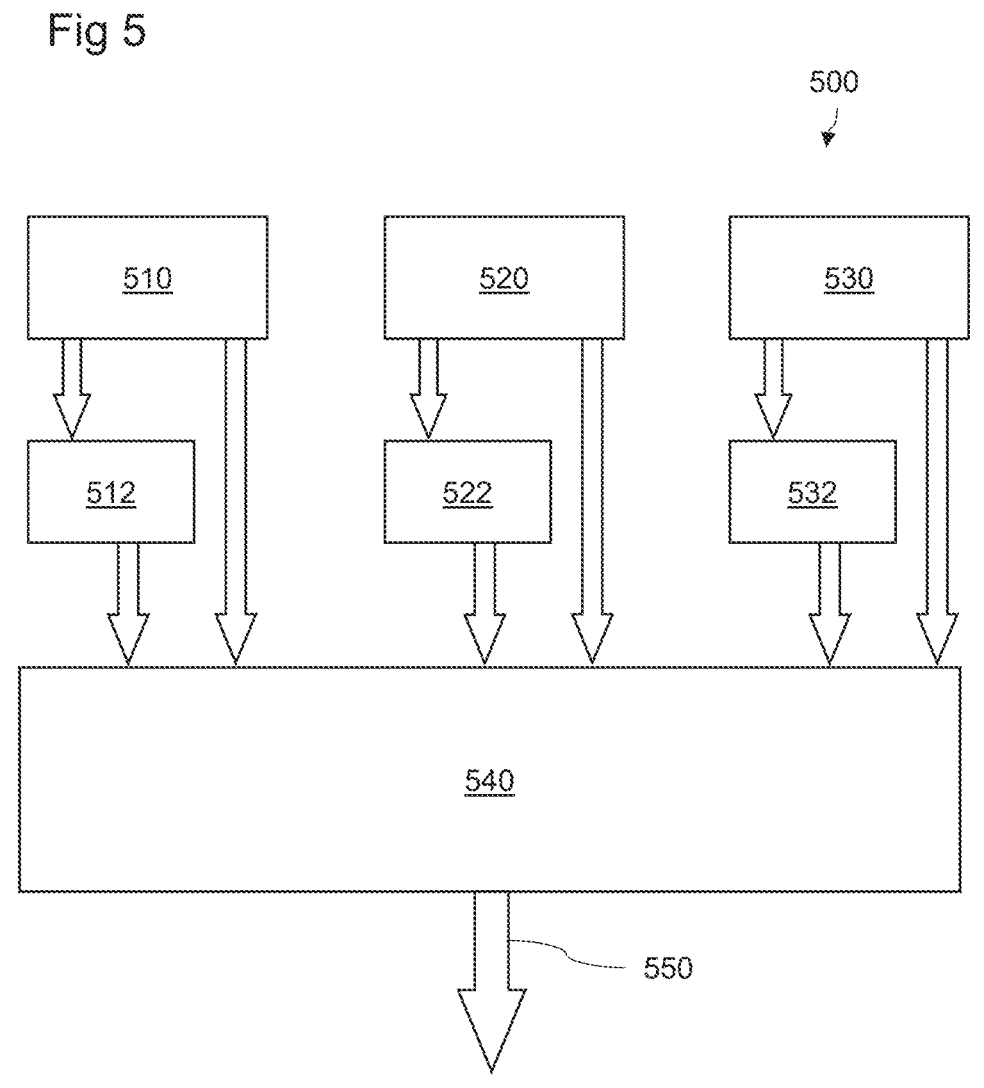

FIG. 5 represents schematically an example method 500 of determining visual parameter data for a sample point in a rendering process for rendering a volumetric dataset and/or a radiation dose distribution in the volumetric dataset. The method 500 may, for example, be applied in a rendering process as described above with reference to FIGS. 2 and 3.

At block 510, the value of the volumetric dataset at the sample point is determined, e.g. by interpolating the volumetric dataset at the sample point location. At block 512, a transfer function is applied to the determined value of the volumetric dataset at the sample point to determine volume visualization parameter data, such as color and opacity information and values for material properties for the sample point. Determining the volume visualization parameter data may also include performing a shading computation.

At block 520, a material type associated with the sample point is determined. For example, a segmentation mask for the volumetric dataset may have been determined which indicates the type or types of material represented by different parts of the volumetric dataset. From this segmentation mask, a material type, e.g. a type of organ or tissue, at the sample point may be determined. At block 522, a transfer function is applied to the material type to determine segmentation visualization parameter data for the sample point.

At block 530, a radiation dose value at the sample point is determined. This radiation dose value may be determined as described in examples above, e.g. by computing the radiation dose contributions at the sample point from one or more radiation sources, or, alternatively, by performing a lookup for a radiation dose value for the sample point in a radiation dose map. At block 532, a transfer function is applied to the radiation dose value to obtain radiation visualization parameter data for the sample point.

At blocks 512, 522, 532, the respective transfer functions applied may be window-levelled transfer functions. The visual parameter data provided by the transfer functions at 512, 522, 532 may comprise for example, one or more of color and visibility-related parameter values (e.g. opacity or alpha values) and values for parameters relating to material properties such as roughness, refraction, phase function, etc.

The volume visualization parameter data, the segmentation visualization parameter data and the radiation visualization parameter data output by the transfer function applied at 512, 522 and 532 form inputs to a combination module 540, as represented in FIG. 5 by the arrows from the blocks 512, 522, 532 to the combination module 540. As is represented by the arrows in FIG. 5 directly connecting the blocks 510, 520, 530, the combination module 540 may also receive as inputs the volume data, segmentation data and dose data. The combination module 540 is arranged to determine and to output, at 550, visual parameter data for the sample point based on the received inputs.

For example, the combination module 540 may blend one or more of the volume visualization parameter data, the segmentation visualization parameter data and the radiation visualization parameter data. The visual parameter data 550 may comprise one or more of an opacity, a color, and material properties for the sample point.

The combination module 540 may allow for arbitrary combinations of the volume visualization parameter data, the segmentation visualization parameter data and the radiation visualization parameter data. For example, the volume visualization parameter data may comprise RGBA colors and shading data for the sample point in the volumetric dataset and the combination module 540 may provide for this information derived from the volumetric dataset (e.g. from the CT/MR scan data) to be combined in various ways with the information derived from the segmentation and dose values.

For example, the combination module 540 may provide for clipping of the volumetric dataset information (i.e. the anatomy information) while not clipping the dose information.

The combination module 540 may provide for ensuring that particular anatomical features are shown in the visualization by use of the segmentation data.

The combination module 540 may apply special material properties to particular anatomical features, e.g. by use of the segmentation data. For example, a glass rendering effect may be applied for skin, where sample points representing skin are identified by the segmentation data.

The combination module 540 may filter from the visualization dose information and/or anatomy information (i.e, the volumetric dataset) and/or segmented anatomical structures selectively. The combination module 540 may achieve this, for example, by combining the opacity or alpha values for the volume visualization parameter data, the segmentation visualization parameter data and the radiation visualization parameter data in an appropriate manner, for example multiplying or performing any other mathematical operation on the opacity values.

The combination module 540 may colorize the sample point based on a volume color and/or segmentation color and/or dose color output, respectively, by the transfer functions 512, 522, 532.

The combination module 540 may in some examples derive reflective and/or refractive properties for the sample point from the volume visualization parameter data and/or segmentation visualization parameter data and/or dose visualization parameter data. The combination module 540 may be configured to provide various visual effects by the reflective and/or refractive properties. For example, the combination module 540 may be configured to provide a glass shell effect. Such an effect may allow nearly unoccluded views on a target region in the volumetric dataset while providing for anatomical context to be provided by the visualization. In one specific example, to prevent visual distortions, a refractive index of the material being visualized can be set to a value of 1, to provide a transparent plastic foil visual effect.

The method 500 allows for a wide variety of visualization styles and may, for example, be used to mitigate occlusion of certain features in a visualization of the volumetric dataset and/or radiation dose distribution, for example, as described above, by interactive filtering of anatomy based on the determined radiation dose and/or by applying special visual effects such as a glass effect to certain anatomical features.

The method allows for the fusion of many data sources and for visual parameter data for the sample point to be computed based on said data sources. The parameters of the transfer function or the manner in which the combination module produces the visual parameter data for the sample point may be interactively changed in order to customize the visualization. By applying the method 500 to determine visual parameter data for sample points in a rendering method, e.g. a physically-based rendering method, radiation dose information and anatomical information can be visualized in a manner which preserves anatomical context while removing anatomy which is not relevant to the visualization. E.g. an area such as a tumor which is simulated to receive a high radiation dose can be visualized, while surrounding structures which may occlude the visualization of the tumor can be removed from the visualization, e.g. by filtering from the visualization those structures which receive radiation doses below a given threshold or by rendering those structures in a transparent manner.

Figure 6:
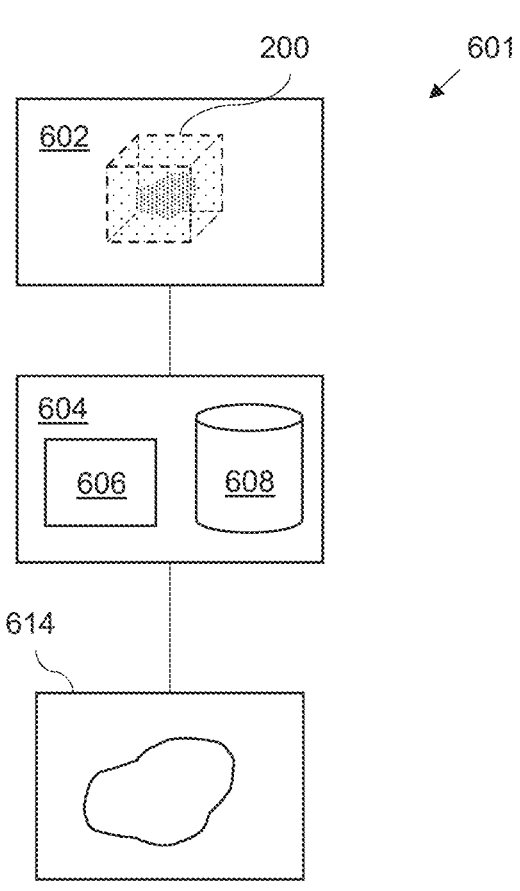
FIG. 6 shows an apparatus for performing example methods described herein.

Referring now to FIG. 6, there is illustrated schematically an example system 601 in which an example apparatus 604 may use methods described herein. The system 601 comprises a scanner 602, the apparatus 604, and a visualization unit 614. In examples, the system may comprise fewer components than or additional components to those illustrated in FIG. 6. For example, the system 601 may comprise a computer network such as the internet.

The scanner 602 may be any scanner for generating a dataset comprising the volumetric dataset 200, which, as described may, for example, be a medical volumetric dataset representing a portion of a patient. For example, the scanner 602 may be a computed tomography (CT) scanner, a magnetic resonance imaging (MRI) scanner, a positron emission tomography (PET) scanner, an ultrasound scanner or the like. In another example the scanner 602 may, for example, be for producing a volumetric dataset representing geological data. The scanner 602 is connected to the apparatus 604, for example via wired or wireless connection. The scanner 602 may be arranged to provide the volumetric dataset to the apparatus 604.

The apparatus 604 comprises a processor 606 and a memory, in the form of a storage (or storage device) 608. The apparatus 604 may, for example comprise a GPU. In this example, the apparatus 604 is arranged to perform the above described method of determining a radiation dose distribution for the volumetric dataset.

The apparatus 604 may for example, comprise a processor for operating a volume rendering process. The volume rendering process may comprise simulating light transport within the volumetric dataset 200. For example, the volume rendering process may comprise a direct volume rendering process, e.g. ray casting. Alternatively, or additionally, the volume rendering process may comprise a physically-based rendering process, e.g. involving a Monte Carlo path tracing method.

In other examples, the method of determining the radiation dose distribution and rendering of the volumetric dataset and/or of the radiation dose distribution may be performed by different apparatuses.

The storage 608 may comprise a machine-readable medium comprising a set of machine-readable instructions which when executed by the processor 606 cause the apparatus 604 to perform an example method described herein. The program may be stored on a computer readable medium which may be read by the apparatus 604 to thereby execute the program. The apparatus 604 may be arranged to receive directly or indirectly or otherwise acquire from the scanner 602 the volumetric dataset 200.

The apparatus 604 may be arranged to transmit information, for example, radiation dose values, and/or a color value for each pixel in an image plane, to a visualization unit 614. The transmission may be direct or indirect, for example via a wired connection, a wireless connection, or via the internet.

The visualization unit 614 may comprise visualization software for displaying a two-dimensional projection of the volume 200 produced by the apparatus 604. The visualization unit 614 may comprise a display screen, and one or more graphics hardware or software components. In some examples, the visualization unit 614 may be or comprise a mobile device. In some examples the visualization unit 614 may comprise a virtual reality or augmented reality device. The visualization unit 614 may display a stereo image.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code.

Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The above embodiments are to be understood as illustrative examples of the present invention. Other embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the present invention, which is defined in the accompanying claims.

What is claimed is:

1. A computer-implemented method for use in determining a radiation dose distribution in a medical volume, the computer-implemented method comprising:

performing a selection process of a rendering process for generating a visualization of a volumetric dataset, the volumetric dataset including voxels, the selection process including selecting at least one sample point in the volumetric dataset on which to perform a radiation dose determination process, the selection process including sampling a path at intervals of one or more sample points per voxel, the one or more sample points being among the at least one sample point, the voxel being among the voxels, and the volumetric dataset representing the medical volume; and performing the radiation dose determination process to determine a radiation dose at each of the at least one sample point.

2. The computer-implemented method of claim 1, wherein the selection process includes:

determining one or more paths through the volumetric dataset for use in the rendering process; and selecting one or more points along each of the one or more paths as the at least one sample point.

3. The computer-implemented method of claim 2, wherein the determining determines the one or more paths according to a physically-based path tracing process or a ray casting process.

4. The computer-implemented method of claim 2, wherein the radiation dose determination process includes determining a radiation dose contribution at each of the at least one sample point from each of one or more radiation sources located at one or more corresponding positions with respect to the volumetric dataset.

5. The computer-implemented method of claim 2, wherein the radiation dose determination process includes determining the radiation dose at each of the at least one sample point based on a dose map associated with the volumetric dataset.

6. The computer-implemented method of claim 2, wherein the at least one sample point includes a plurality of sample points; and the performing the radiation dose determination process includes determining the radiation dose distribution in the volumetric dataset without computing a volumetric dose map for the volumetric dataset.

7. The computer-implemented method of claim 1, wherein the radiation dose determination process includes determining a radiation dose contribution at each of the at least one sample point from each of one or more radiation sources located at one or more corresponding positions with respect to the volumetric dataset.

8. The computer-implemented method of claim 7, wherein the determining of the radiation dose contribution at each of the at least one sample point from a first radiation source among the one or more radiation sources includes simulating an arrival at the at least one sample point of attenuated radiation from the first radiation source.

9. The computer-implemented method of claim 8, wherein the at least one sample point includes a plurality of sample points; and the performing the radiation dose determination process includes determining the radiation dose distribution in the volumetric dataset without computing a volumetric dose map for the volumetric dataset.

10. The computer-implemented method of claim 7, wherein the determining of the radiation dose contribution from a first radiation source among the one or more radiation sources includes simulating radiation arriving at each of the at least one sample point from the first radiation source by one or more scattered radiation paths.

11. The computer-implemented method of claim 10, wherein the at least one sample point includes a plurality of sample points; and the performing the radiation dose determination process includes determining the radiation dose distribution in the volumetric dataset without computing a volumetric dose map for the volumetric dataset.

12. The computer-implemented method of claim 7, wherein the at least one sample point includes a plurality of sample points; and the performing the radiation dose determination process includes determining the radiation dose distribution in the volumetric dataset without computing a volumetric dose map for the volumetric dataset.

13. The computer-implemented method of claim 1, wherein the radiation dose determination process includes determining the radiation dose at each of the at least one sample point based on a dose map associated with the volumetric dataset.

14. The computer-implemented method of claim 7, wherein the at least one sample point includes a plurality of sample points; and the performing the radiation dose determination process includes determining the radiation dose distribution in the volumetric dataset without computing a volumetric dose map for the volumetric dataset.

15. The computer-implemented method of claim 1, wherein the at least one sample point includes a plurality of sample points; and the computer-implemented method further comprises performing the rendering process to render the visualization of at least one of the volumetric dataset or the radiation dose distribution, the radiation dose distribution including the radiation dose at each of the plurality of sample points.

16. The computer-implemented method of claim 15, wherein a sampling resolution of the plurality of sample points is equal to a sampling resolution of the rendering process.

17. The computer-implemented method of claim 16, wherein the rendering process includes determining a visual parameter value for each of the plurality of sample points for use in the rendering process based on one or more of:

the radiation dose at each of the plurality of sample points;

a value of the volumetric dataset at each of the plurality of sample points; or a segmentation associated with each of the plurality of sample points.

18. The computer-implemented method of claim 17, wherein the rendering process comprises:

determining a respective radiation dose visualization parameter value associated with each of the plurality of sample points based on the radiation dose at each of the plurality of sample points to obtain a plurality of radiation dose visualization parameter values;

determining a respective volume visualization parameter value associated with each of the plurality of sample points based on the value of the volumetric dataset at each of the plurality of sample points to obtain a plurality of volume visualization parameter values; and combining the plurality of radiation dose visualization parameter values and the plurality of volume visualization parameter values to determine the visual parameter value of each of the plurality of sample points.

19. The computer-implemented method of claim 15, wherein the rendering process includes determining a visual parameter value for each of the plurality of sample points for use in the rendering process based on one or more of:

the radiation dose at each of the plurality of sample points;

a value of the volumetric dataset at each of the plurality of sample points; or a segmentation associated with the plurality of sample points.

20. The computer-implemented method of claim 19, wherein the rendering process comprises:

determining a respective radiation dose visualization parameter value associated with each of the plurality of sample points based on the radiation dose at each of the plurality of sample points to obtain a plurality of radiation dose visualization parameter values;

determining a respective volume visualization parameter value associated with each of the plurality of sample points based on the value of the volumetric dataset at each of the plurality of sample points to obtain a plurality of volume visualization parameter values; and combining the plurality of radiation dose visualization parameter values and the plurality of volume visualization parameter values to determine the visual parameter value of each of the plurality of sample points.

21. The computer-implemented method of claim 15, wherein the rendering process includes filtering from the visualization sample points at which the radiation dose is at or below a threshold value among the plurality of sample points.

22. The computer-implemented method of claim 1, wherein the at least one sample point includes a plurality of sample points; and the performing the radiation dose determination process includes determining the radiation dose distribution in the volumetric dataset without computing a volumetric dose map for the volumetric dataset.

23. A non-transitory computer-readable storage medium storing machine-readable instructions that, when executed by one or more processors, cause the one or more processors to perform the computer-implemented method according to claim 1.

24. An apparatus comprising:

at least one processor; and a storage device storing a set of machine-readable instructions that, when executed by the at least one processor, cause the apparatus to perform the computer-implemented method according to claim 1.

25. An apparatus for determining a radiation dose distribution in a medical volume, the apparatus comprising:

at least one processor; and a storage device storing a set of machine-readable instructions that, when executed by the at least one processor, cause the apparatus to perform a selection process of a rendering process for generating a visualization of a volumetric dataset, the volumetric dataset including voxels, the selection process including selecting at least one sample point in the volumetric dataset on which to perform a radiation dose determination process, the selection process including sampling a path at intervals of one or more sample points per voxel, the one or more sample points being among the at least one sample point, the voxel being among the voxels, and the volumetric dataset representing the medical volume, and perform the radiation dose determination process to determine a radiation dose at each of the at least one sample point.

26. A computer-implemented method for use in determining and visualizing a radiation dose distribution in a medical volume, the computer-implemented method comprising:

receiving a volumetric dataset representing the medical volume;

performing a volume rendering process including performing a selection process to select one or more sample points in the volumetric dataset, and performing first operations for each respective sample point of the one or more sample points in the volumetric dataset, the first operations including determining a volume visualization parameter value based on a value of the volumetric dataset at the respective sample point, determining a radiation dose visualization parameter value based on a determined a radiation dose at the respective sample point, and determining a respective visual parameter value based on the radiation dose visualization parameter value and the volume visualization parameter value at the respective sample point; and rendering a visualization of the volumetric dataset and the radiation dose distribution using the respective visual parameter values of the one or more sample points.

* * * * *